United States Patent
Akutsu et al.

(10) Patent No.: US 6,169,260 B1
(45) Date of Patent: Jan. 2, 2001

(54) APPARATUS FOR MELTING A NEEDLE USING AN ELECTRIC CURRENT

(75) Inventors: Naoji Akutsu; Yukio Ota, both of Tokyo (JP)

(73) Assignee: Oki Data Corporation, Tokyo (JP)

( * ) Notice: Under 35 U.S.C. 154(b), the term of this patent shall be extended for 0 days.

(21) Appl. No.: 09/274,688

(22) Filed: Mar. 24, 1999

(30) Foreign Application Priority Data

Apr. 3, 1998 (JP) .................................................. 10-091117

(51) Int. Cl.$^7$ ........................... B23K 11/22; A61G 12/00; A61L 11/00
(52) U.S. Cl. ............................................................. 219/68
(58) Field of Search ............................... 219/68; 439/11, 439/13, 29, 30

(56) References Cited

U.S. PATENT DOCUMENTS

| | | | |
|---|---|---|---|
| 4,870,311 | * 9/1989 | Chase et al. ............................ | 439/13 |
| 4,961,541 | * 10/1990 | Hashimoto ............................. | 219/68 |
| 5,468,928 | 11/1995 | Yelvington ............................. | 219/68 |
| 5,545,869 | * 8/1996 | Piva ....................................... | 219/68 |
| 5,676,859 | 10/1997 | Yanobu .................................. | 219/68 |
| 5,852,267 | * 12/1998 | Yanobu .................................. | 219/68 |
| 6,051,802 | * 4/2000 | Davis et al. ........................... | 219/68 |

FOREIGN PATENT DOCUMENTS

| | | |
|---|---|---|
| 0 913 163 | 5/1999 | (EP) . |
| WO 93/25250 | 12/1993 | (WO) . |

* cited by examiner

Primary Examiner—Geoffrey S. Evans
(74) Attorney, Agent, or Firm—Rabin & Champagne PC

(57) ABSTRACT

A needle disposal apparatus for melting a needle to be disposed of by passage of electrical current through it, has a guide member having an inlet which permits the needle to be inserted; an upper electrode roller, to which a first voltage is applied, the inserted needle making contact with an outer surface of the upper electrode roller; a lower electrode roller to which a second voltage is applied, the inserted needle making contact with an outer surface of the lower electrode roller; and a drive mechanism which rotates the electrode rollers in each direction so that the inserted needle is drawn between the electrode rollers; wherein the electrode rollers are disposed so that a part of the lower electrode roller is hidden behind the upper electrode roller when viewed from the inlet in a direction of insertion of the needle.

13 Claims, 5 Drawing Sheets

APPARATUS FOR MELTING A NEEDLE USING AN ELECTRIC CURRENT

BACKGROUND OF THE INVENTION

The present invention relates to a needle disposal apparatus which melts and disposes of a needle such as a used needle of a hypodermic syringe.

A conventional needle disposal apparatus is often of a fixed electrode type, as shown in FIG. 9. The needle disposal apparatus of this type has fixed electrode plates 21 and 22, between which a given voltage is applied by a power source 23. Heat is produced in a used needle 24 of a hypodermic syringe 25 by passage of electrical current between the electrode plates 21 and 22 through the needle 24, thereby melting the needle 24. However, contact areas 21a and 22a in the electrode plates 21 and 22, with which the needle 24 is in contact, become oxidized to form an oxide of high resistance, resulting in a disadvantage that the needle disposal apparatus loses its melting action after disposal of several tens to several hundreds of needles.

To overcome this disadvantage, a needle disposal apparatus having rotatable electrode rollers 36 and 41 as shown in FIG. 10 is developed. In FIG. 10, a reference numeral 31 denotes a battery as a power source, 32 denotes a power switch with a breaker, 33 denotes a fastened terminal, and 34 denotes an insulator bushing. Further, reference numerals 35 and 44 denote contact blades which are disposed in contact with contact areas on the rotary shafts 38 and 43 supporting the electrode rollers 36 and 41. The blades 35 and 44 are formed of phosphor bronze with a thickness of 0.3 mm.

The upper electrode roller 36 is mounted on a case 50 (shown by two-dotted broken lines) by a pair of bearings 37 disposed on the opposite sides thereof so as to be rotatable and is electrically insulated from the case 50. On its one end, the rotary shaft 38 of the upper electrode roller 36 is fixedly provided with a gear 39b which is engaged with a gear 40a on a shaft of a motor 40 so as to be rotated in a direction $A_1$ by driven power transmitted from the motor 40. The rotary shaft 38 of the upper electrode roller 36 is also provided with a gear 39a which is engaged with a gear 41a fixedly mounted on the rotary shaft 43 of the lower electrode roller 41. Thus the lower electrode roller 41 is rotated by the driven power transmitted from the motor 40 in a direction $A_2$ opposite to the direction $A_1$.

The lower electrode roller 41 is rotatably supported on the case 50 by a pair of bearings 42. The rotary shaft 43 of the lower electrode roller 41 has a contact area on one of its axial ends which is disposed in contact with the contact blade 44 which is connected to a battery terminal of the opposite polarity from the terminal which is connected to the contact blade 35. Each electrode roller 36 and 41 is formed of a brass cylindrical member with chrome plating.

FIG. 11 illustrates a needle to be disposed of and electrode rollers in the apparatus of FIG. 10. In FIG. 10, when the used needle 24 is brought into contact with both the upper electrode roller 36 and the lower electrode roller 41, current of a high magnitude flows through the needle 24. Therefore, the stainless steel needle is heated to cause its melt-down.

It is possible that oxide films of high resistance be formed on the surfaces of the upper electrode roller 36 and the lower electrode roller 41 or that a contamination may be deposited on the needle 24 to interface with the current conduction therethrough. However, even in such instance, the surface of the needle 24 is mechanically scrubbed by the electrode rollers 36 and 41 which are rotating, whereby such oxide films are removed. Thus the arrangement of FIG. 10 eliminates a failure of melt-down which may be caused by oxide film as in the arrangement of FIG. 9.

However, the needle disposal apparatus having rotating electrodes mentioned above still suffers from a number of shortcomings as indicated below.

1. A heating which occurs between the contact blade 35 (or 44) and the contact area of the rotary shaft 38 (or 43) may result in a loss of resilience in the phosphor bronze.
2. As the contact area of the rotary shaft 38 (or 43) becomes abraded and oxidized, its fragments may be deposited around the contact area of the rotary shaft 38 (or 43) to cause a poor contact. A contact formed between dissimilar metals is essentially liable to cause a poor contact. The fragments are in turn scrubbed as may be typified by abrasion due to minimal sliding motion to produce insulating oxides, representing insulative dregs, which then find their way into the contact region to increase a resistance of contact, contributing to a further heating. This ultimately results in a poor contact.
3. A hypodermic needle has a varying thickness from 16 G (having a diameter ø of 1.6 mm) to 30 G (having a diameter ø of 0.3 mm). Where the needle is inserted between the pair of electrode rollers 36 and 41 as in the prior art practice where the electrode rollers 36 and 41 abut laterally against the needle 24, an accommodation for a varying thickness of the needle has been unsatisfactory. An accommodation employed with the arrangement of FIG. 10 has been to provide a variation in the thickness or the diameter of the upper electrode roller 36 from location to location. However, with this technique, a user must slide the needle in a direction $B_1$ of an axis of the electrode roller 33 to determine the position where it is inserted manually in accordance with the thickness thereof, which is cumbersome. If the electrode rollers 36 and 41 are abraded, a satisfactory contact is no longer ensured, with consequence that the useful life of the electrode rollers 36 and 41 is limited to the order of several thousands of needles which can be disposed of.

In addition, if a needle having an increased thickness is strongly and rapidly urged into the interstice between the pair of electrode rollers 36 and 41, there results an insufficient amount of heating to melt down the needle, which would then be flexed to be fitted between the upper roller 36 and the lower roller 41. In worst cases, the needle may not be withdrawn from between the electrode rollers 36 and 44.

4. Both the upper and the lower electrode rollers 36 and 44 are of an equal diameter and are driven to rotate at an equal rotational speed, thus presenting a substantially equal resistance of contact. This resulted in a failure to melt down the needle at a definite position thereon. In other words, when viewed from the standpoint of the quality of disposal, it is difficult to keep the length of the needle which remains without being melted down constant. Thus if the needle is melted down at the point of contact with the lower electrode roller 41, the remaining length will be lower. By contrast, if the needle is melted down at the point of contact with the upper electrode roller 36, the length of the residue will be relatively short, but a plastic body of the syringe will be scorched to cause a stench.

5. A needle disposal apparatus is constructed on the premise that it melts down the hypodermic needle. It is to be noted however that needles are of varying types, including one which has its surface coated with a plastic. Such a needle does not allow a current conduction and hence cannot be melted down. If such a needle is inserted into the apparatus, it will be drawn into the space between the electrode rollers 36 and 41 as the latter rotate without being melted down, thus causing a locked condition of the motor. If the battery is nearly exhausted, the breaker cannot be operated and thus the motor is also likely to be locked.

SUMMARY OF THE INVENTION

It is an object of the present invention to provide a needle disposal apparatus which overcomes various shortcomings mentioned above by enabling a disposal in a facilitated and reliable manner.

According to one aspect of the present invention, a needle disposal apparatus for melting a needle to be disposed of by passage of electrical current through the needle, the apparatus comprises: a guide member having an inlet which permits the needle to be inserted; a first electrode roller formed of a material with electrical conductivity, a first voltage being applied to the first electrode roller, the inserted needle making contact with an outer surface of the first electrode roller; a second electrode roller formed of a material with electrical conductivity, a second voltage which is different from the first voltage being applied to the second electrode roller, the inserted needle making contact with an outer surface of the second electrode roller; and a drive mechanism which rotates the first electrode roller and the second electrode roller in each direction so that the inserted needle is drawn between the first electrode roller and the second electrode roller; wherein the first electrode roller and the second electrode roller are disposed so that a part of the second electrode roller is hidden behind the first electrode roller when viewed from the inlet of the guide member in a direction of insertion of the needle.

Further, the first electrode roller and the second electrode roller rotate in each direction so that the inserted needle is drawn into an interstice between the first electrode roller and the second electrode roller.

Furthermore, the first electrode roller may be disposed so that a lateral surface of the needle inserted from the inlet of the guide member makes contact with the outer surface of the first electrode roller; the second electrode roller may be disposed so that a tip of the needle inserted from the inlet of the guide member makes contact with the outer surface of the second electrode roller; and a point on the outer surface of the second electrode roller with which the tip of the needle makes contact is between a highest position from a reference plane, which is perpendicular to the direction of insertion of the needle and includes a center axis of the second electrode roller, and a position which has a distance in a direction parallel to the reference plane from the center of the second electrode roller, said distance being 71% of a radius of the second electrode roller.

Furthermore, a circumferential velocity of the second electrode roller is greater than a circumferential velocity of the first electrode roller.

Moreover, the needle disposal apparatus may further comprise: a detector which detects that the needle is inserted into the inlet of the guide member; and a controller which controls the drive mechanism so that the first electrode roller and the second electrode roller begin to rotate when the insertion of the needle is detected and stop rotating when a predetermined time has passed from the insertion of the needle.

According to another aspect of the present invention, a needle disposal apparatus for melting a needle to be disposed of by passage of electrical current through the needle, the apparatus comprises: at least one electrode roller formed of a material with electrical conductivity, the needle making contact with an outer surface of the electrode roller; a rotary shaft formed of a material with electrical conductivity, the rotary shaft supporting the electrode roller; a sleeve formed of a material with electrical conductivity and having an opening, the rotary shaft being fitted into the opening; and a contact member formed of a material with electrical conductivity and including a V-shaped groove which maintains contact with an outer surface of the sleeve so as to permit rotation of the rotary shaft together with the sleeve.

Further, the sleeve may be formed of an alloy of silver, and a surface of the V-shaped groove may be formed of an alloy of silver similar to the sleeve.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

Further scope of applicability of the present invention will become apparent from the detailed description given hereinafter. However, it should be understood that the detailed description and specific examples, while indicating preferred embodiments of the present invention, are given by way of illustration only, since various changes and modifications will become apparent to those skilled in the art from the detailed description.

First Embodiment

Figure 1:
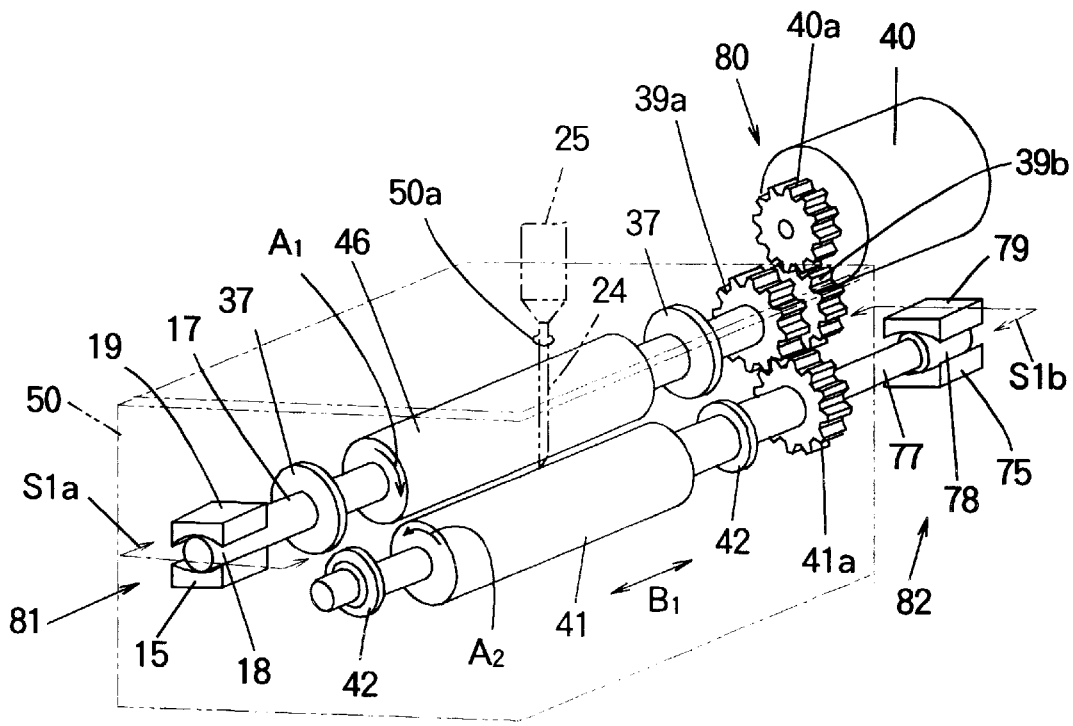
FIG. 1 is a perspective view schematically showing a needle disposal apparatus according to a first embodiment of the present invention.
Figure 2:
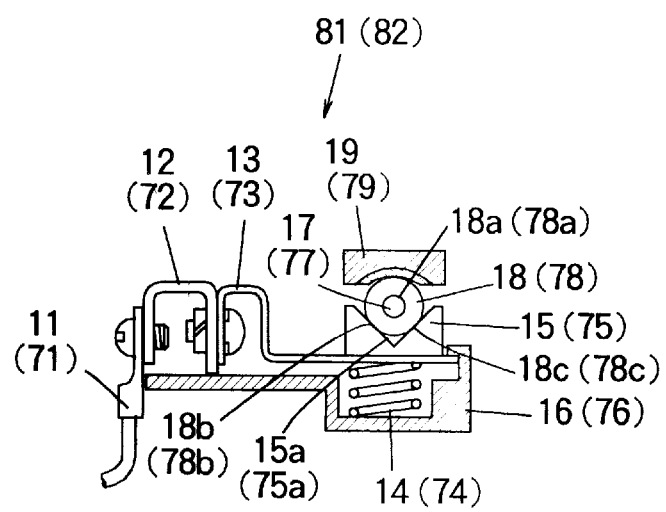
FIG. 2 is a vertical cross-sectional view showing a contact structure of the needle disposal apparatus of FIG. 1.

FIG. 1 is a perspective view schematically showing a needle disposal apparatus according to a first embodiment of the present invention, and FIG. 2 is a vertical cross-sectional view schematically showing a contact structure of the needle disposal apparatus of FIG. 1 when viewed along a direction of an arrow $S_{2a}$ or $S_{2b}$.

Referring to FIG. 1, a needle disposal apparatus according to the first embodiment has a guide member as a part of a case 50 which has an inlet 50a for permitting a needle 24 of a used hypodermic syringe 25 to be inserted thereinto. Further, the guide member may be a separate member fixed to the case 50. The needle disposal apparatus also has an upper electrode roller 46 formed of a material with electrical conductivity, a lower electrode roller 41 formed of a material with electrical conductivity, and a drive mechanism 80 which rotates the upper electrode roller 46 and the lower electrode roller 41 in each direction $A_1$ and $A_2$ so that the inserted needle 24 is drawn into an interstice between the upper electrode roller 46 and the lower electrode roller 41. Each electrode roller 46 and 41 is formed of a brass cylindrical member with chrome plating, for instance. The needle disposal apparatus further has an upper contact structure 81 and a lower contact structure 82.

Referring to FIG. 1 and FIG. 2, the upper contact structure 81 includes an upper rotary shaft 17 which is rotatably supported by a pair of bearings 37 fixed to the case 50, is formed of a material with electrical conductivity, and supports the upper electrode roller 46. Referring to FIG. 2, the upper contact structure 81 also has a sleeve 18 which is formed of an alloy of silver with electrical conductivity and has an opening 18a, into which the upper rotary shaft 17 is firmly press-fitted, a contact member 15 which is formed of an alloy of silver similar to the sleeve 18 and maintains contact with an outer surface of the sleeve 18 so as to permit rotation of the upper rotary shaft 17 together with the sleeve 18. The contact member 15 has a V-shaped groove 15a which extends in a direction $B_1$ of an axis of the upper rotary shaft 17. An area or areas of the contact member 15 maintaining contact with the outer surface of the sleeve 18 is an inner surface of the V-shaped groove 15a of the contact member 15. The rotary shaft 17 as an electrical contact is disposed in concentric relationship with the electrode roller 46.

Further, the lower contact structure 82 has the same components as those in the upper contact structure 82. Referring to FIG. 2, the lower contact structure 82 has a lower rotary shaft 77 which is formed of a material with electrical conductivity and supports the lower electrode roller 41. The lower contact structure 82 also has a sleeve 78 which is formed of an alloy of silver with electrical conductivity and has an opening, into which the rotary shaft 77 is firmly press-fitted, and a contact member 75 which is formed of an alloy of silver similar to the sleeve 78 and maintains contact with an outer surface of the sleeve 78 so as to permit rotation of the rotary shaft 77 together with the sleeve 78. The contact member 75 has a V-shaped groove 75a which extends in a direction $B_1$ of an axis of the rotary shaft 77. An area or areas of the contact member 75 maintaining contact with the outer surface of the sleeve 78 is an inner surface of the V-shaped groove 75a of the contact member 75. The rotary shaft 77 as an electrical contact is disposed in concentric relationship with the electrode roller 41.

Furthermore, in FIG. 2, reference numerals 11 and 71 denote a crimped terminal to which a wiring leading to a battery (not shown) is connected, reference numerals 12 and 72 denote an abutment having one arm which is connected to the terminal 11 (or 71), reference numerals 13 and 73 denote a springy connection plate connected to the abutment 12 (or 72) and having a reduced thickness which is formed of phosphor bronze or brass, reference numerals 14 and 74 denote a spring disposed below the connection plate 13 (or 73) to support it from below, and reference numerals 19 and 79 denote stoppers which bear against the sleeve 18 (or 78). The contact members 15 and 17 are brazed to the upper surface of the connection plates 13 and 73, respectively.

In the above described needle disposal apparatus, a first voltage is applied by the battery (not shown) to the upper electrode roller 46, and a lateral surface of the inserted needle 24 makes contact with an outer surface of the upper electrode roller 46. Further, a second voltage, which is different from the first voltage (for example, a ground voltage) is applied to the lower electrode roller 41 formed of a material with electrical conductivity. A tip of the inserted needle 24 makes contact with an outer surface of the lower electrode roller 41.

In operation, as a power switch (not shown) of the needle disposal apparatus is turned on, the upper electrode roller 46 and the lower electrode roller 41, which may be simply referred to as "electrode rollers", begin to rotate and a predetermined voltage is applied between them. If a needle 24 is inserted from the inlet 50a of the case 50 and the needle 24 makes contact with the electrode rollers 46 and 41, there occurs a current flow through the needle 24. The current flows from a battery (not shown) through the cable (not shown), the crimped terminal 11, the abutment 12, the connection plate 13, the contact member 15 with the V-groove 15a, the sleeve 18, the rotary shaft 17, the upper electrode roller 46, the needle 24, the lower electrode roller 41, the rotary shaft 77, the sleeve 78, the contact member 75 with the V-groove 75a, the connection plate 73, the abutment 72, the crimped terminal 71, and the cable (not shown), for instance.

During the melt-down operation, molten fragments are liable to be deposited on the electrode rollers 46 and 41. If the molten fragments are large, they find their way into the interstice between the electrode rollers 46 and 41, whereby the rotary shafts 17 and 77 of the electrode rollers 46 and 41 may oscillate both vertically and laterally. In this embodiment, the combination of the contact member 15 (or 75) with the V-groove 15a (or 75a), the connection plate 13 (or 73a), and the spring 14 (or 74a) is effective to absorb such oscillations. In this manner, a reliable contact is maintained between the sleeve 18 (or 78) associated with the rotary shaft 17 (or 77) of the electrode roller 46 (or 41) and the V-groove 15a (or 75a) of the contact member 15 (75). Therefore, the probability for the occurrence of a poor contact can be more reliably prevented by providing a pair of such combinations which are suspended independently from each other.

While the contact member has been constructed with a base metal in the prior art, in the present embodiment, the contact members 15 and 75 and the sleeves 18 and 78 are constructed as a contact pair structure using similar noble metals such as an alloy of silver, which avoids a difference in the ionization tendency between them, whereby an oxide hardly forms if a high current flows. Accordingly, if the contact is subject to a sliding motion, there results a less likelihood that an insulating oxide is scraped out between the contact members 15 and 75 and the sleeves 18 and 78 to cause a poor contact.

In addition, the V-groove 15a (or 75a) of the contact member 15 (or 75) in accordance with the present embodiment is disposed in contact with the sleeve 18 (or 78) at two points 18b and 18c (or 78b and 78b), as shown in FIG. 2, and the force acting upon either points of the outer surface of the sleeve 18 (or 78) which differ by about 90° from each other. Accordingly, for an oscillation occurring in any direction, the pressure of contact acting upon at least one of the areas of contact will be increased. If foreign matters such as dusts find their way into the interstice between the contact formed by the V-groove 15a (or 75a) of the contact member 15 (or 75), they will migrate toward the bottom of the V-groove 15 (or 75), and will stay between the contacts for a reduced length of time. The contacting integrity of the contacts is rapidly recovered, thus enhancing the reliability of the contacts.

It is said that a contact between similar metals is susceptible to abrasion because of the same hardness. However, in actuality, such abrasion occurs only for the initial phase. If fragments or dregs are produced by the abrasion, they are less likely to be converted into insulating oxides because the contact is formed in the present embodiment by using noble medals, i.e. an alloy of silver. As mentioned previously, if oxides are produced, the oxides produced rapidly move into the bottom of the V-groove 15a (or 75a) and cannot remain in the area of contacts. In this manner, a stabilized contact can be maintained in accordance with the present embodiment.

Because the sleeves 18 and 78 and the rotary shafts 17 and 77 are formed of dissimilar metals, a press fit construction is used for the junction therebetween. This isolates the junction from air to inhibit the formation of oxide and also inhibits an abrasion due to minimal sliding motion therebetween. The use of an adhesive therebetween is avoided, thus preventing any resistance added. As a consequence, there is obtained an ideal contact assembly which produces a reduced heating if a high current, which may be on the order of 150 amperes in the present embodiment, flows. It is found that when the contact assembly is formed using an adhesive such as a silver paste to proved a junction between the both members for purpose of comparison, there occurred an increased amount of heating, which caused the adhesion to be broken, eventually causing an abrasion of the sleeve due to minimal sliding movement to result in a poor contact.

It is to be understood that the contact structures 81 and 82 mentioned above in connection with the first embodiment are not limited in its application to a needle disposal apparatus, but is also applicable to an actuator of higher current level since the connection terminal provides an enhanced reliability in feeding a higher current to a working area.

Second Embodiment

Figure 3:
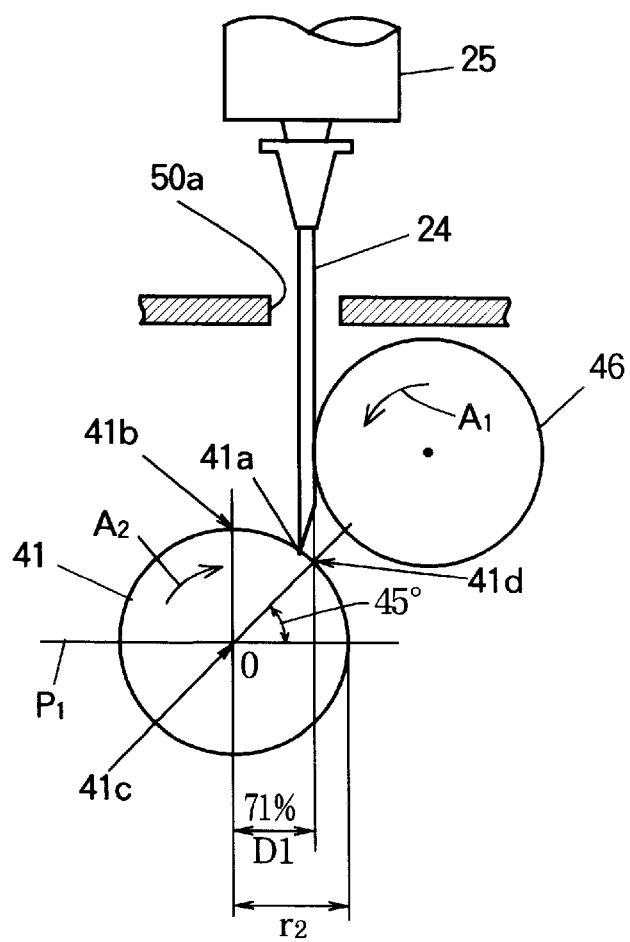
FIG. 3 is a schematic view showing electrode rollers of a needle disposal apparatus according to a second embodiment of the present invention.
Figure 9:
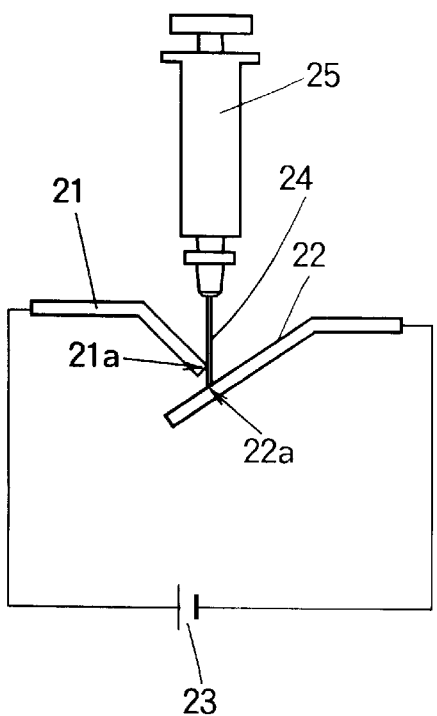
FIG. 9 is a schematic view showing a conventional needle disposal apparatus.

FIG. 3 is a schematic view showing electrode rollers of a needle disposal apparatus according to a second embodiment of the present invention. The second embodiment is principally characterized in the positional relationship of the upper electrode roller 46, the lower electrode roller 41, and the inlet 50a of a needle. In other respects, the fundamental construction is similar to the prior art shown in FIG. 9 or the needle disposal apparatus of FIG. 1. The characterizing relationship according to the second embodiment, as shown in FIG. 3, will be described below.

Referring to FIG. 3, in the second embodiment, the upper electrode roller 46 and the lower electrode roller 41 are disposed so that a part of the lower electrode roller 41 is hidden behind the upper electrode roller 46 when viewed from the inlet 50a provided in the case 50 in a direction of insertion of the needle 24 and the needle 24 makes contact with both the upper electrode roller 46 and the lower electrode roller 41. To be precise, the upper electrode roller 46 is disposed so that a lateral surface of the needle 24 inserted from said inlet 50a makes contact with the outer surface of the upper electrode roller 46. The lower electrode roller 41 is disposed so that a tip of the needle 24 inserted from the inlet 50a makes contact with the outer surface of the lower electrode roller 41. In the second embodiment, a point 41a on the outer surface of the lower electrode roller 41 with which the tip of the needle 41 makes contact is between a highest position 41b from a reference plane $P_1$, which is perpendicular to the direction of insertion of the needle 24 and includes a center axis 41c of said second electrode roller 41, and a position 41d which has a distance $D_1$, which is 71% of a radius $r_2$ of the lower electrode roller 41, in a direction parallel to the reference plane $P_1$ from the center 41c of the lower electrode roller 41.

It is to be understood that the inlet 50a may be formed so that a needle 24 can be inserted in an oblique direction with reference to the vertical direction. In this case, the reference plane $P_1$ is set to be perpendicular to the direction of such insertion. Further, the upper electrode roller 46 and the lower electrode roller 41 rotate toward each other, as indicated by arrows Al and $A_2$, and rotate at the same rotational speed.

It is to be understood that the drive mechanism 80 which rotates the upper electrode roller 46 and the lower electrode roller 41 is similar to that used in the prior art (FIG. 10) or the first embodiment (FIG. 1).

In operation, when the power switch (not shown) of the needle disposal apparatus is turned on and the motor 40 drives the upper electrode roller 46 and the lower electrode roller 41 to rotate toward each other and the needle 24 is inserted through the inlet 50a, it will be seen that a tip of the needle 24 will abut against the lower electrode roller 41 (this is referred to as "tip abutment"). Because the lower electrode roller 41 is rotating clockwise (the direction $A_2$) as shown, the tip of the needle 24 is urged toward the upper electrode roller 46 while it is maintained in contact with the outer surface of the lower electrode roller 41. The lateral surface of the needle 24 now contacts the upper electrode roller 46. The surface of the needle 24 is scraped by the rotating electrode rollers 46 and 41 in its regions where it is in contact with these electrode rollers 46 and 41, and the conduction of the electrical current causes a high current flow between the electrode rollers 46 and 41. The both electrode rollers 46 and 41 are formed of brass and have a sufficiently greater thickness than the needle 24 and thus present a lower resistance. By contrast, the needle 24 which is formed of stainless steel presents a higher resistance. In addition, the surface of the needle 24 is formed with a passivation film inherent to the stainless steel, and thus presents a greater resistance of contact. Accordingly, a heating occurs in the needle 24 principally in the region of contact with the electrode rollers 46 and 41, and the needle 24 is eventually melted down to drop as a liquid. Molten fragments are centrifuged by the rotation of the electrode rollers 46 and 41 to fall down in a path between the electrode rollers 46 and 41, partly also involving a sputtering as a result of a rapid melting. When the needle 24 which has its tip melted down is further depressed, a fresh portion thereof will be again brought into contact with the electrode rollers 46 and 41 to be subject to a melting action in the same manner as mentioned above. Such operation is repeated, and the needle 24 will be ultimately melted down in its entirety except for a portion thereof which cannot reach the lower electrode roller 41.

Figure 10:
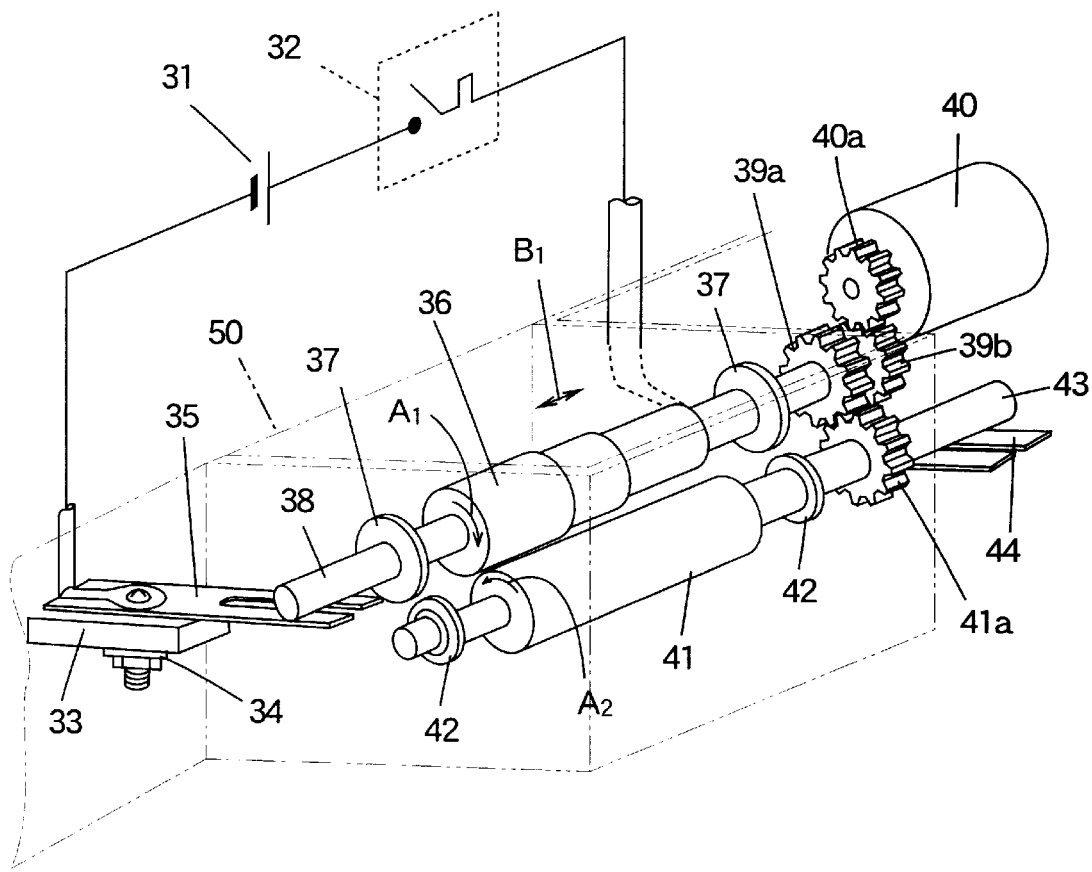
FIG. 10 is a perspective view schematically showing another conventional needle disposal apparatus.
Figure 11:
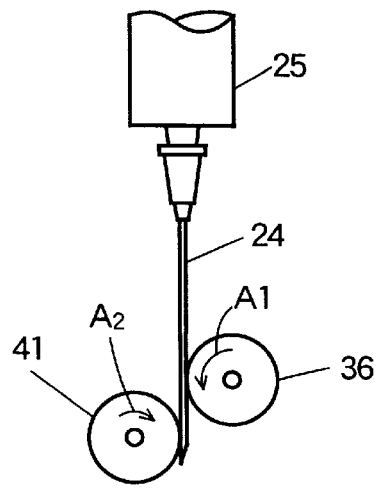
FIG. 11 is a schematic view showing a needle to be disposed of and electrode rollers of FIG. 10.

As discussed above, with the needle disposal apparatus according to the second embodiment, the tip of the needle 24 is always brought into abutment against the outer surface of the lower electrode roller 41 within a range between a highest position 41b from a reference plane $P_1$ and a position 41d which has a distance $D_1$, which is 71% of a radius $r_2$ of the lower electrode roller 41, in a direction parallel to the reference plane $P_1$ from the center 41c, and subsequently the lateral surface of the needle 24 is urged by the rotation of the lower electrode roller 41 into abutment against the upper electrode roller 46. Accordingly, the needles of a varying thickness can be disposed of. There is no need for a troublesome operation of displacing the inlet 50a in accordance with the diameter of the needle. Further, there is no need to provide a roller having a plurality of diameters as in the prior art (FIG. 10). In addition, if the upper electrode roller 46 becomes abraded, such abrasion has little influence upon the melting disposal, and hence the arrangement has a substantially increased useful life.

By limiting the point of abutment of the needle tip against the lower electrode surface 41 within a range between a highest position 41b from a reference plane $P_1$ and a position 41d which has a distance $D_1$ in a direction parallel to the reference plane $P_1$ from the center 41c (at an angle of 45° with respect to the center 41c), it is assured that if the needle 24 is rapidly inserted, the tip of the needle 24 is always brought in the abutment against the lower electrode roller 41 and cannot be further inserted. There is no occurrence that the needle 24 becomes entangled between the electrode rollers 46 and 41 without being melted down. In this manner, the occurrence of a failure to melt down the needle 24, the occurrence of a needle residue or the occurrence of an entanglement to prevent its removal are eliminated, assuring a stabilized melting operation.

Except for the points described above, the apparatus of the second embodiment is the same as that of the prior art (FIG. 10) or the first embodiment (FIG. 1).

Third Embodiment

Figure 4:
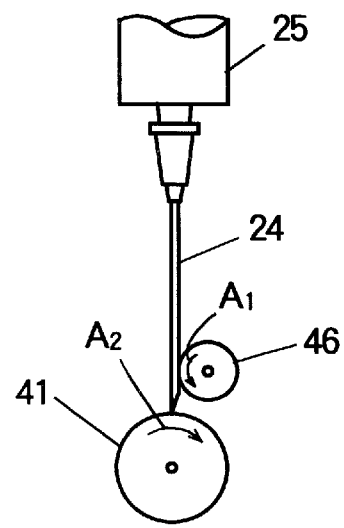
FIG. 4 is a schematic view showing electrode rollers of a needle disposal apparatus according to a third embodiment of the present invention.
Figure 5:
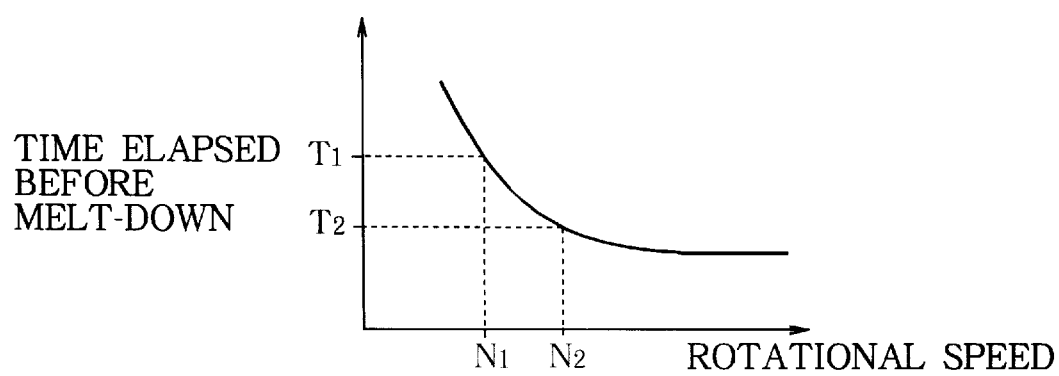
FIG. 5 graphically shows a relationship between the time that elapsed before the melt-down and the rotational speed of the electrode roller in the third embodiment.

FIG. 4 is a schematic view showing electrode rollers of a needle disposal apparatus according to a third embodiment of the present invention, and FIG. 5 graphically shows a relationship between the time that elapsed before the melt-down and the rotational speed of the electrode roller in the third embodiment. In the third embodiment, the ratio of radii of the upper electrode roller 46 and the lower electrode roller 41 is different from that of the second embodiment.

In the third embodiment, the lower electrode roller 41 has a diameter ø of 8 mm while the upper electrode roller 46 has a diameter ø of 6 mm. The electrode rollers 46 and 41 rotate at the same rotational speed and toward each other, as indicated by arrows $A_1$ and $A_2$. A ratio of circumferential velocities for the electrode rollers 41 and 46 is equal to 4:3, whereby the lower electrode roller 41 has a speed which is by about 33% higher.

To describe the operation, reference is made to FIG. 4 which illustrates a relationship between the time elapsed before the melt-down and the rotational speed when the upper and the lower electrode rollers 46 and 41 of an equal diameter are driven for rotation at the same speed. It will be seen from FIG. 4 that the higher the rotational speed of the electrode rollers 46 and 41, the higher the melt-down capability. It will also be noted that the melt-down capability becomes constant and cannot increase any further at or greater than a given rotational speed. This means that the arrangement according to the present invention, that is, the rotation of the electrode rollers is effective. The choice of the circumferential velocity of the surface of the lower electrode roller 41 higher than the circumferential velocity of the surface of the upper electrode roller 46 is equivalent to saying that the melt-down performance of the lower electrode roller 41 is higher than that of the upper electrode roller 46. In other words, the melt-down operation can be substantially entirely performed by the lower electrode roller 41.

Thus in the third embodiment, the melt-down operation principally takes place by the lower electrode roller 41 by the choice of a higher circumferencial velocity therefor. This means that a variation which occurs in the location where the melt-down occurs is reduced. Accordingly, the occurrence of a large variation in the location of melt-down to cause a longer residue or a short residue which causes a scorching of a plastic body is eliminated. In addition, a most efficient value can be selected for the rotational speed of the electrode roller.

There may be a concern that an abrasion of the electrode rollers 46 and 41 attributable to a scraping with the needle 24 may cause an increase in the length of residue of the needle 24. However, the melt-down by the lower electrode roller 41 takes place electrically, and the lower electrode roller 41 is little subject to abrasion. It is pointed out that the abrasion occurs as a result of no melting action, and thus the abrasion occurs in the upper electrode roller 46 in a concentrated manner. If the upper electrode roller 46 becomes abraded, the lower electrode roller 41 remains without abrasion, whereby the distance as measured from the surface of the lower electrode roller 41 to the center (or contact) of the upper electrode roller 46 remains unchanged and thus the length of the residue does not change. In other words, the needle disposal apparatus according to the third embodiment provides a melt-down performance which remains stabilized over a prolonged length of time.

In the third embodiment, a greater diameter is chosen for the lower electrode roller 41, but, both the upper and lower electrode rollers 46 and 41 may have an equal diameter, and a suitable gear ratio may be chosen to provide a more rapid rotation of the lower electrode roller 41.

Except for the points described above, the apparatus of the third embodiment is the same as that of the first or second embodiment.

Fourth Embodiment

Figure 6:
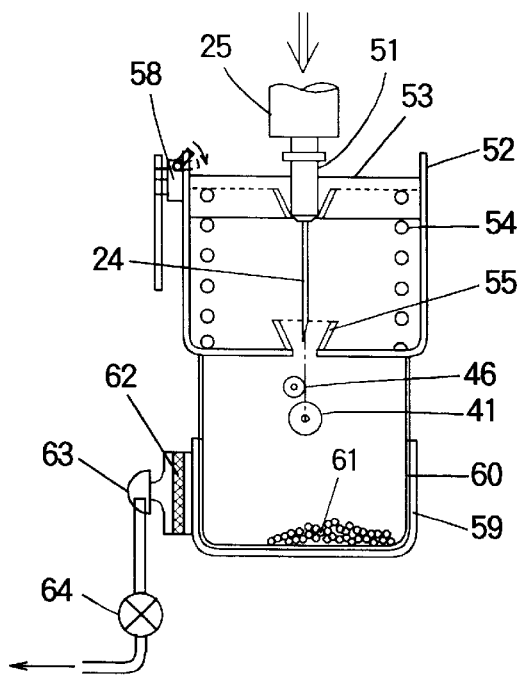
FIG. 6 is a schematic view of a needle disposal apparatus according to a fourth embodiment of the present invention.
Figure 7:
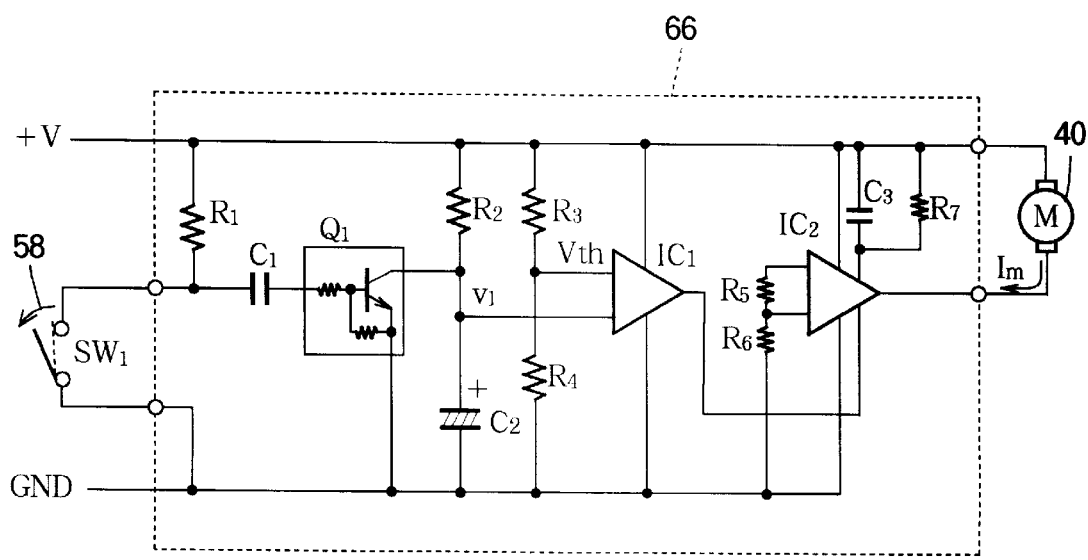
FIG. 7 is a circuit diagram showing a control circuit of the needle disposal apparatus of FIG. 6.

FIG. 6 is a schematic view of a needle disposal apparatus according to a fourth embodiment of the present invention, and FIG. 7 is a circuit diagram of a control circuit of the needle disposal apparatus of FIG. 6. In this embodiment, a needle 24 of a hypodermic syringe 25 is inserted through an inlet of a float 53 which moves up and down within a cylinder 52 and is depressed against the resilience of a spring 54 so that it is passed through an insertion guide 55 to be subject to a melt-down operation by a combination of a lower electrode roller 41 and an upper electrode roller 46.

Molten fragments 61 are accumulated inside an aluminum foil 60 disposed along the inside of a dust box 59, thereby presenting no problem if they fall in an incandescent condition. Powder dust and stench are absorbed by an activated carbon filter 62, thus allowing only clean air to be discharged through an outlet 63 by a pump 64. As the syringe 25 is depressed, the float 53 releases a sensor switch 58, a signal from which opens a switch $SW_1$ shown in the circuit diagram of FIG. 6, thus allowing the motor 40 to be set in motion to begin rotating the electrode rollers 46 and 41. It is to be noted that all the elements in this circuit inclusive of comparators $IC_1$ and $IC_2$ constitute together an analog circuit.

Figure 8:
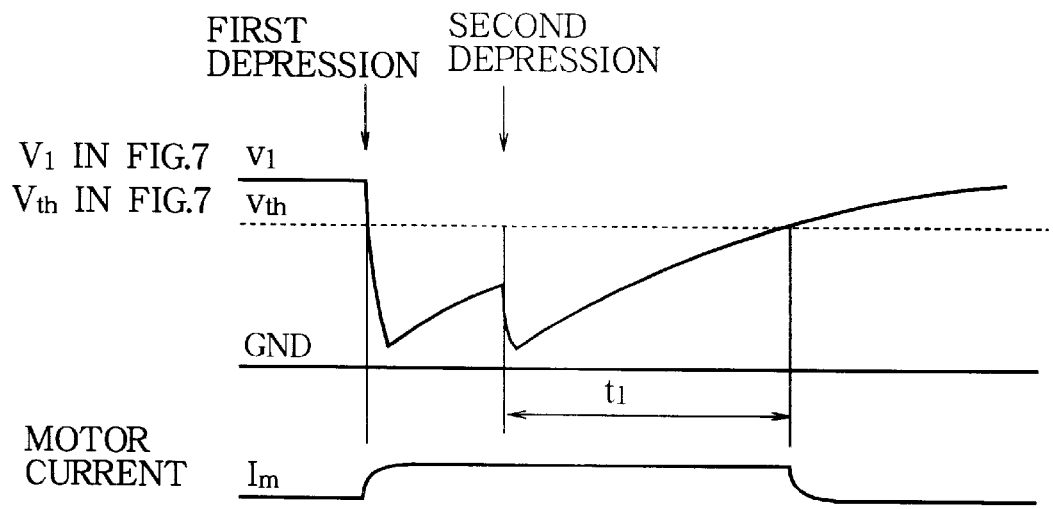
FIG. 8 is a series of timing charts illustrating the timings of operation of the needle disposal apparatus of FIG. 6.

FIG. 8 is a series of timing charts illustrating the timings of operation of the needle disposal apparatus of FIG. 6. As shown, in the present embodiment, when the switch $SW_1$ is opened, that is, the sensor switch 58 is released, the motor 40 is set in motion for about $t_1$ seconds. If the float 53 moves up and down again during $t_1$ seconds of operation of the motor 40, it is retriggered to operate for $t_1$ seconds from that time.

Thus the needle disposal apparatus according to the fourth embodiment is constructed such that as the needle 24 of the hypodermic syringe 25 is inserted, the motor current Im begins to flow so that the motor 40 begins to operate and continues to operate for a given interval of $t_1$ seconds, and then the motor 40 is automatically stopped. This enables a prevention of noises during a stand-by condition and a reduction in the power dissipation. The needle disposal apparatus of the fourth embodiment is simple to operate because there is no need to operate the switch each time. If a needle covered by a plastic or a foreign matter is inserted into the apparatus, the latter is automatically stopped after a given time interval, thus providing a safeguard of the apparatus. Because the control circuit 66 is an analog circuit, the possibility that a malfunctioning is caused by noises which may be produced as a result of a flow of a high current during the melt-down operation is reduced, thus enhancing the reliability.

In the fourth embodiment, the control circuit 66 comprises analog elements. However, the circuit may be replaced by a microcomputer provided a safeguard against the malfunctioning of a logic circuit due to noises is provided.

Except for the points described above, the apparatus of the third embodiment is the same as that of any one of the first to third embodiments.

The invention being thus described, it will be obvious that the same may be varied in many ways. Such variations are not to be regarded as a departure from the spirit and scope of the invention, and all such modifications as would be obvious to one skilled in the art are intended to be included within the scope of following claims.

What is claimed is:

1. A needle disposal apparatus for melting a needle to be disposed of by passage of electrical current through the needle, said apparatus comprising:
    a guide member having an inlet which permits the needle to be inserted;
    a first electrode roller formed of a material with electrical conductivity, a first voltage being applied to said first electrode roller, the inserted needle making contact with an outer surface of said first electrode roller;
    a second electrode roller formed of a material with electrical conductivity, a second voltage which is different from the first voltage being applied to said second electrode roller, the inserted needle making contact with an outer surface of said second electrode roller; and
    a drive mechanism which rotates said first electrode roller and said second electrode roller so that the inserted needle is drawn between said first electrode roller and said second electrode roller;
    wherein said first electrode roller and said second electrode roller are disposed so that a part of said second electrode roller is hidden behind said first electrode roller when viewed from said inlet of said guide member in a direction of insertion of the needle.

2. The needle disposal apparatus of claim 1, wherein said first electrode roller and said second electrode roller rotate so that the inserted needle is drawn into an interstice between said first electrode roller and said second electrode roller.

3. The needle disposal apparatus of claim 1, wherein:
    said first electrode roller is disposed so that a lateral surface of the needle inserted from said inlet of said guide member makes contact with the outer surface of said first electrode roller;
    said second electrode roller is disposed so that a tip of the needle inserted from said inlet of said guide member makes contact with the outer surface of said second electrode roller; and
    a point on the outer surface of said second electrode roller with which the tip of the needle makes contact is between a highest position from a reference plane, which is perpendicular to the direction of insertion of the needle and includes a center axis of said second electrode roller, and a position which has a distance in a direction parallel to the reference plane from the center of said second electrode roller, the distance being 71% of a radius of said second electrode roller.

4. The needle disposal apparatus of claim 1, wherein a circumferential velocity of said second electrode roller is greater than a circumferential velocity of said first electrode roller.

5. The needle disposal apparatus of claim 1, further comprising:
    a detector which detects that the needle is inserted into said inlet of said guide member; and
    a controller which controls said drive mechanism so that said first electrode roller and said second electrode roller begin to rotate when the insertion of the needle is detected and stop rotating when a predetermined time has passed from the insertion of the needle.

6. The needle disposal apparatus of claim 1, further comprising:
    a first rotary shaft formed of a material with electrical conductivity and supporting said first electrode roller;
    a first sleeve formed of a material with electrical conductivity and having a first opening, said rotary shaft being fitted into said first opening of said first sleeve; and
    a first contact member formed of a material with electrical conductivity and including a first V-shaped groove which maintains contact with an outer surface of said first sleeve so as to permit rotation of said first rotary shaft together with said first sleeve.

7. The needle disposal apparatus of claim 6, wherein said first sleeve is formed of an alloy of silver, and a surface of said first V-shaped groove is formed of an alloy of silver similar to said first sleeve.

8. The needle disposal apparatus of claim 6, further comprising:
    a second rotary shaft formed of a material with electrical conductivity and supporting said second electrode roller;
    a second sleeve formed of a material with electrical conductivity and having a second opening, said second rotary shaft being fitted into said second opening of said second sleeve; and
    a second contact member formed of a material with electrical conductivity and including a second V-shaped groove which maintains contact with an outer surface of said second sleeve so as to permit rotation of said second rotary shaft together with said second sleeve.

9. The needle disposal apparatus of claim 8, wherein said second sleeve is formed of an alloy of silver, and a surface of said second V-shaped groove is formed of an alloy of silver similar to said second sleeve.

10. The needle disposal apparatus of claim 1, further comprising:
    a rotary shaft formed of a material with electrical conductivity and supporting said second electrode roller;
    a sleeve formed of a material with electrical conductivity and having an opening, said rotary shaft being fitted into said opening of said sleeve; and a contact member formed of a material with electrical conductivity and including a V-shaped groove which maintains contact with an outer surface of said second sleeve so as to permit rotation of said rotary shaft together with said sleeve.

11. The needle disposal apparatus of claim 10, wherein said sleeve is formed of an alloy of silver, and a surface of said V-shaped groove is formed of an alloy of silver similar to said sleeve.

12. A needle disposal apparatus for melting a needle to be disposed of by passage of electrical current through the needle, said apparatus comprising:

at least one electrode roller formed of a material with electrical conductivity, the needle making contact with an outer surface of said electrode roller;

a rotary shaft formed of a material with electrical conductivity and supporting said electrode roller, said rotary shaft extending horizontally;

a sleeve formed of a material with electrical conductivity and having an opening, said rotary shaft being fitted into said opening, said sleeve being disposed at an end of said rotary shaft;

a contact member formed of a material with electrical conductivity and including a V-shaped groove which maintains contact with an outer surface of said sleeve so as to permit rotation of said rotary shaft together with said sleeve, said V-shaped groove having a depth that is greatest directly below said sleeve;

a stopper disposed directly above said sleeve, and bearing against said sleeve; and a member which exerts force for lessening a space between said contact member and said stopper.

13. A needle disposal apparatus for melting a needle to be disposed of by passage of an electrical current through the needle, said apparatus comprising:

at least one electrode roller formed of a material with electrical conductivity, the needle making contact with an outer surface of said electrode roller;

a rotary shaft formed of a material with electrical conductivity and supporting said electrode roller;

a sleeve formed of a material with electrical conductivity and having an opening, said rotary shaft being fitted into said opening; and a contact member formed of a material with electrical conductivity and including a V-shaped groove which maintains contact with an outer surface of said sleeve so as to permit rotation of said rotary shaft together with said sleeve, wherein said sleeve is formed of an alloy of silver, and a surface of said V-shaped groove is formed of an alloy of silver similar to said sleeve.

* * * * *